United States Patent [19]

Koike et al.

[11] Patent Number: 5,278,340
[45] Date of Patent: Jan. 11, 1994

[54] OLIGOHEXAFLUOROPROPYLENE OXIDE DERIVATIVE AND PROCESS OF PRODUCING THE SAME

[75] Inventors: Noriyuki Koike, Yoshii; Masayuki Oyama, Takasaki; Toshio Takago, Annaka, all of Japan

[73] Assignee: Shin-Etsu Chemical Co., Ltd., Tokyo, Japan

[21] Appl. No.: 903,967

[22] Filed: Jun. 26, 1992

[30] Foreign Application Priority Data

Jun. 28, 1991 [JP] Japan .................. 3-183564

[51] Int. Cl.⁵ ............................................. C07C 51/04
[52] U.S. Cl. .................................... 562/853; 562/848; 568/677
[58] Field of Search ................................ 562/853

[56] References Cited

U.S. PATENT DOCUMENTS

| | | | |
|---|---|---|---|
| 3,250,807 | 5/1966 | Fritz et al. | 562/853 |
| 3,250,808 | 5/1966 | Moore, Jr. et al. | |
| 3,322,826 | 5/1967 | Moore | 562/853 |

FOREIGN PATENT DOCUMENTS

| | | |
|---|---|---|
| 0151877 | 8/1985 | European Pat. Off. |
| 0472422 | 2/1992 | European Pat. Off. |
| 1570964 | 3/1970 | Fed. Rep. of Germany |
| 998978 | 7/1965 | United Kingdom |

OTHER PUBLICATIONS

Abstract of Japanese Kokai Tokkyo Koho 63-30441 1985.

Primary Examiner—Paul J. Killos
Attorney, Agent, or Firm—Oblon, Spivak, McClelland, Maier & Neustadt

[57] ABSTRACT

Oligohexafluoropropylene oxide derivatives represented by the general formula (I):

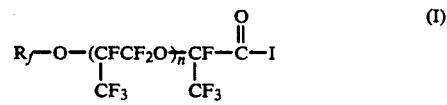

wherein $R_f$ represents a perfluoroalkyl group having 1 to 10 carbon atoms and n is an integer of 0 to 100 or the general formula (II):

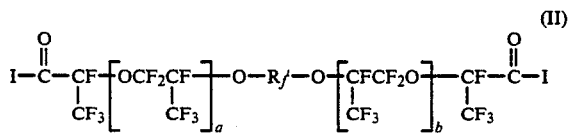

wherein $R_f'$ represents a perfluoroalkylene group having 2 to 10 carbon atoms and a and b are each independently an integer of 0 to 20. These compounds are novel and are useful as intermediates for synthesizing iodine-containing oligohexafluoropropylene oxides useful as raw materials for fluororesins, fluororubbers, and fluorine-containing surfactants.

7 Claims, 10 Drawing Sheets

OLIGOHEXAFLUOROPROPYLENE OXIDE DERIVATIVE AND PROCESS OF PRODUCING THE SAME

BACKGROUND OF THE INVENTION

1. Field of the Invention

The present invention relates to a novel oligohexafluoropropylene oxide derivative useful for the synthesis of fluororesins, fluororubbers, fluorine-containing surfactants, etc. and a process of producing the same.

2. Description of the Prior Art

An industrially applicable process of producing iodine-containing oligohexafluoropropylene oxides represented by the general formula (i):

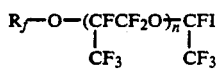

wherein $R_f$ represents a perfluoroalkyl group having 1 to 10 carbon atoms and n is an integer of 0 to 100 and the general formula (ii):

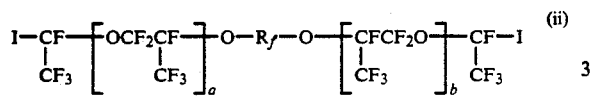

wherein $R_f'$ represents a perfluoroalkylene group having 2 to 10 carbon atoms and a and b are each independently an integer of 0 to 20 which are conventionally intermediates for synthesizing fluoroesins, fluororubbers, fluorine-containing surfactants, etc. is not known yet.

That is, hitherto, for example, to produce an iodine-containing oligohexafluoropropylene oxide of the general formula (i), a process is known wherein first, as is shown below, an oligohexafluoropropylene oxide carboxylic acid fluoride represented by the general formula (iii) used as a raw material is hydrolyzed to obtain a carboxylic acid (iv), then the carboxylic acid (iv) is converted to the silver salt (v) using silver oxide, and the silver salt (v) is thermally decomposed in the presence of $I_2$ to obtain the iodine-containing oligohexafluoropropylene oxide of the general formula (i) (Japanese Pre-examination Patent Publication (kokai) No. 63-30441 (1988):

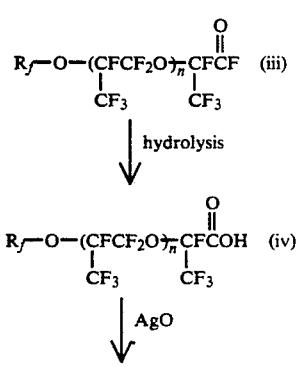

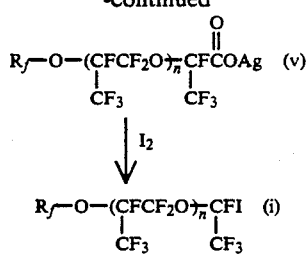

However, according to the above process, the yield of the intended iodine-containing oligohexafluoropropylene oxide (i) is about 70 to 85%. Further, in most of the cases, the silver salt that is an intermediate is solid, which means that the handling is difficult, and in addition there is a defect that since expensive silver is used, recovery of the silver is necessary where the process is industrially employed. Further, where the process is performed industrially, many problems are involved, for example, the process includes 3 steps, hydrogen fluoride which is toxic is given off during the process, and a thermal decomposition reaction is necessary for obtaining the intended product. There are also such disadvantages that, in view of the cost, expensive raw materials are used and the cost of facilities increases.

Therefore, it is demanded to produce an iodine-containing oligohexafluoropropylene oxide of the general formula (i) industrially advantageously without such problems.

SUMMARY OF THE INVENTION

The present inventor has keenly studied in various ways to answer the above demand and has found that by reacting the oligohexafluoropropylene oxide carboxylic acid fluoride corresponding to the intended compound and a specific metal iodide, a novel oligohexafluoropropylene oxide derivative having a carbonyl iodide group is obtained easily in high yield without by-products even under atmospheric pressure at room temperature, and by irradiating the derivative with ultraviolet light at room temperature, carbon monoxide is given off from the derivative to give the intended iodine-containing oligohexafluoropropylene oxide of the general formula (i) or (ii) with a high conversion without generating any by-product.

Therefore, an object of the present invention is to provide such a novel oligohexafluoropropylene oxide derivative and a process of producing the same.

Novel Oligohexafluoropropylene Oxide Derivatives

That is, according to the present invention, there is provided an oligohexafluoropropylene oxide derivative represented by the general formula (I):

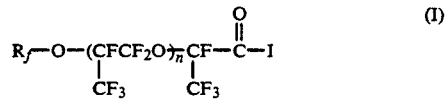

wherein $R_f$ represents a perfluoroalkyl group having 1 to 10 carbon atoms and n is an integer of 0 to 100.

Further, according to the present invention, there is provided an oligohexafluoropropylene oxide derivative represented by the general formula (II):

$$\text{I}-\overset{\overset{\text{O}}{\|}}{\text{C}}-\underset{\text{CF}_3}{\text{CF}}-\left[\underset{\text{CF}_3}{\text{OCF}_2\text{CF}}\right]_a-\text{O}-\text{R}_f'-\text{O}-\left[\underset{\text{CF}_3}{\text{CFCF}_2\text{O}}\right]_b-\underset{\text{CF}_3}{\text{CF}}-\overset{\overset{\text{O}}{\|}}{\text{C}}-\text{I} \quad \text{(II)}$$

wherein $R_f'$ represents a perfluoroalkylene group having 2 to 10 carbon atoms and a and b are each independently an integer of 0 to 20.

As is described above, the oligohexafluoropropylene oxide derivatives represented by the formulas provided by the present invention are novel compounds and are useful as intermediates for synthesizing the iodine-containing oligohexafluoropropylene oxides represented by the formulas (i) and (ii) useful as raw materials for fluororesins, fluororubbers, and fluorine-containing surfactants, and according to the present process, the oligohexafluoropropylene oxide derivatives represented by the formulas (I) and (II) can be produced in high yield industrially advantageously.

DETAILED DESCRIPTION OF PREFERRED EMBODIMENTS

Figure 1:
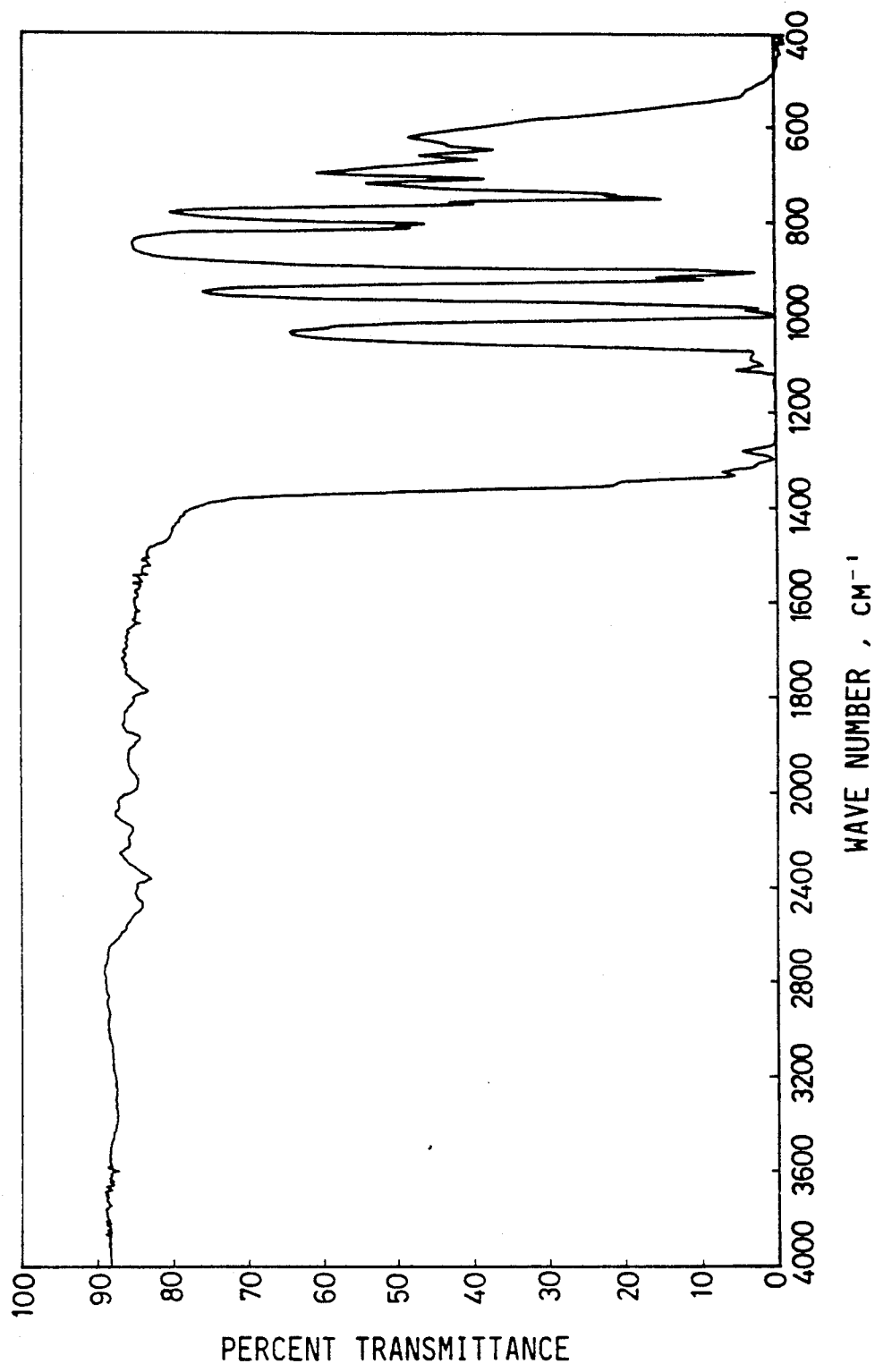
FIG. 1 is the infrared absorption spectrum of Example 1.

In the general formula (I), $R_f$ represents a perfluoroalkyl group having 1 to 10 carbon atoms and specifically represents, for example, a trifluoromethyl group, a pentafluoroethyl group, a heptafluoropropyl group, or a heptafluoroisopropyl group, and n is an integer of 0 to 100 and is generally in the range of 0 to 30. In the formula (II), $R_f'$ represents a perfluoroalkylene group having 2 to 10 carbon atoms and specifically represents, for example, $-CF_2CF_2-$, $-CF_2CF_2CF_2-$, $-CF_2CF_2CF_2CF_2-$ or $-CF_2CF_2CF_2CF_2CF_2-$, and a and b are each independently an integer of 0 to 20 and are each generally in the range of 0 to 10.

When the compounds of the general formulas (I) and (II) are irradiated with ultraviolet light, carbon monoxide is easily given off to produce iodine-containing oligohexafluoropropylene oxides represented by the general formulas (i) and (ii) used as useful intermediates for synthesizing fluororesins, fluororubbers, fluorine-containing surfactants, etc.

In comparison with the above described prior process, the process of producing a compound of the general formula (i) and a compound of the general formula (ii) from a compound of the general formula (I) or the general formula (II) has many advantages, for example, in that (1) the yield of the steps is very high, (2) the process does not use expensive silver oxide, (3) since the process comprises two steps, the steps can be simplified, (4) hydrogen fluoride which is toxic is not given off during the process, (5) the reaction temperature is low, (6) the oligohexafluoropropylene oxide derivative represented by the general formula (I) which is an intermediate is liquid at room temperature and if the oligohexafluoropropylene oxide derivative is low molecular weight, it can be isolated by distillation, and (7) the step where ultraviolet light is radiated requires only the irradiation with the ultraviolet light without requiring any other particular procedure during the irradiation with the ultraviolet light and therefore if a tank for holding the reaction liquid is installed in the apparatus, the scale can be made infinitely large in theory, so that an iodine-containing oligohexafluoropropylene oxide represented by the general formula (i) or (ii) can be produced industrially advantageously. Consequently, the oligohexafluoropropylene oxide derivatives represented by the general formulas (I) and (II) are quite useful as intermediates for synthesizing the compounds represented by the formulas (i) and (ii) respectively.

Process of the Preparation

The compound represented by the general formula (I) can be produced by reacting an oligohexafluoropropylene oxide carboxylic acid fluoride represented by the general formula (III);

$$R_f-\text{O}-(\underset{\text{CF}_3}{\text{CFCF}_2\text{O}})_{\overline{n}}\underset{\text{CF}_3}{\overset{\overset{\text{O}}{\|}}{\text{CFCF}}} \quad \text{(III)}$$

wherein $R_f$ represents a perfluoroalkyl group having 1 to 10 carbon atoms and n is an integer of 0 to 100 and a metal iodide represented by the general formula (IV):

$$MI_c \quad \text{(IV)}$$

wherein M represents a metal atom and c represents the number equal to the valence of said metal atom.

Also the compound of the general formula (II) can be produced by reacting an oligohexafluoropropylene oxide carboxylic acid fluoride represented by the general formula (V):

$$\overset{\overset{\text{O}}{\|}}{\text{FCCF}}-\left[\underset{\text{CF}_3}{\text{OCF}_2\text{CF}}\right]_a-\text{O}-\text{R}_f'-\text{O}-\left[\underset{\text{CF}_3}{\text{CFCF}_2\text{O}}\right]_b-\underset{\text{CF}_3}{\overset{\overset{\text{O}}{\|}}{\text{CFCF}}} \quad \text{(V)}$$

wherein $R_f'$ represents a perfluoroalkylene group having 2 to 10 carbon atoms and a and b are each independently an integer of 0 to 20 and a metal iodide represented by the above general formula (IV).

The above oligohexafluoropropylene oxide carboxylic acid fluoride represented by the general formula (III) or (V) can be produced by a known process (see U.S. Pat. Nos. 3,250,807 and 3,322,826).

Examples of the metal iodide of the general formula (IV) include an alkali metal iodide such as LiI and NaI, an alkali earth metal iodide such as $MgI_2$ and $CaI_2$ and $AlI_3$. The amount of the metal iodide to be used is such that the amount of iodine in the metal iodide is preferably 1 to 1.2 mol per mol of the group represented by the formula:

$$-\underset{\underset{O}{\parallel}}{C}-F$$

which is contained in the oligohexafluoropropylene oxide carboxylic acid fluoride represented by the general formula (III) or (V), and specifically in the case of an alkali iodide, that amount of the iodine is desirably 1 to 1.2 mol and in the case of an alkali earth metal iodide, that amount of the iodine is desirably 0.5 to 0.6 mol.

It is recommended that both of these reactions are carried out in the presence of a polar solvent. For example, a polar solvent is added to the oligohexafluoropropylene oxide carboxylic acid fluoride represented by the general formula (III) or (IV) and a metal iodide is added little by little thereto with stirring.

In this case, as the polar solvent, an aprotic solvent such as diethyl ether, diisopropyl ether, dibutyl ether, and acetonitrile can be preferably used. Where an alkali metal iodide is used, the amount of the polar solvent to be used is preferably 2 to 10 parts by weight per 100 parts by weight of the alkali metal iodide, while where an alkali earth metal iodide is used, the amount of the polar solvent to be used is preferably 4 to 20 parts by weight per 100 parts by weight of the alkali metal iodide. The reaction temperature is 0° to 100° C., preferably 20° to 50° C., and the reaction time is 2 to 50 hours, preferably 5 to 10 hours. In this case, since the raw materials and the products are highly hydrolizable, preferably the inside of the reactor is previously replaced well with an inert gas such as nitrogen and argon. After the completion of the reaction, the produced metal fluoride is removed by filtering, and the solvent is distilled off, so that the present oligohexafluoropropylene oxide derivative represented by the general formula (I) or (II) can be obtained in a high yield (at least 84%).

As described above, when these oligohexafluoropropylene oxide derivatives represented by the general formulas (I) and (II) are irradiated with ultraviolet light, carbon monoxide is easily given off as shown below, so that the respective corresponding iodine-containing oligohexafluoropropylene oxide derivatives represented by the general formulas (i) and (ii) can be obtained in high yield:

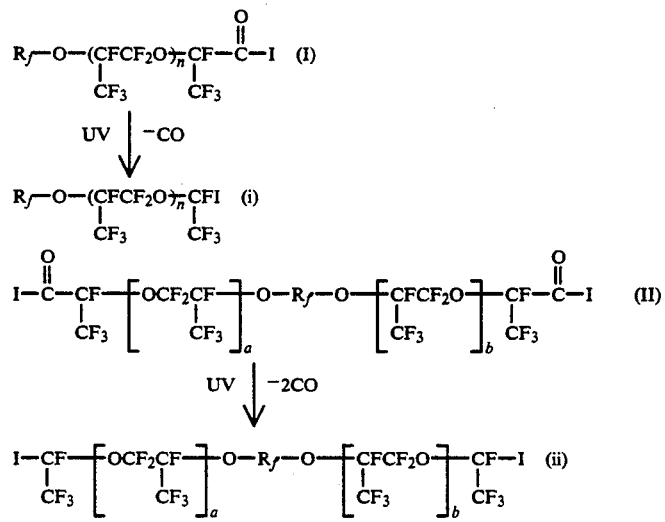

In this case, for the irradiation with ultraviolet light, an ultraviolet-light irradiating apparatus equipped with a high-pressure mercury lamp having a quartz cooling tube can be used. The reaction can be carried out by charging the raw materials into this apparatus and irradiating the raw materials with ultraviolet light of $\lambda=180$ to 380 nm, preferably $\lambda=200$ to 300 nm, at a temperature of 0° to 60° C., preferably at room temperature for 2 to 30 hours. A solvent is not particularly required, but in some cases a stable solvent is added for dilution and the reaction can be carried out. As that organic solvent, perfluoroethane or perfluoroisononane can, for example, be used. This reaction is also preferably carried out under an atmosphere of an inert gas such as nitrogen and argon.

The thus obtained iodine-containing oligohexafluoropropylene oxide derivatives represented by the general formulas (i) and (ii) are useful as intermediates for synthesizing fluororesins, fluororubbers, fluorine-containing surfactants, etc.

EXAMPLES

Now, the present invention will be described specifically with reference to the following Examples, but the present invention is not limited to the Examples.

EXAMPLE 1

A mechanical stirrer, a reflux condenser, and a gas introducing tube were attached to a four-necked flask with an internal volume of 0.5 l. 400 g (0.80 mol) of a carboxylic acid fluoride represented by the following formula:

$$\text{n-C}_3\text{F}_7-\underset{\underset{CF_3}{|}}{O CFCF_2} O \underset{\underset{CF_3}{|}}{CFCOF}$$

wherein n—$C_3H_7$— represents a normal propyl group and 8 g of acetonitrile were charged into the flask. While the contents were stirred, 118 g (0.88 mol) of lithium iodide was added thereto in portions little by little under a flow of argon. At that time, the amount of the lithium iodide added was controlled so that the temperature of the contents might not exceed 40° C. After the completion of the addition, the contents were stirred for about 15 hours.

Then the contents were filtered through a glass filter to remove the solids. The obtained liquid was distilled to obtain 421 g of a product having a boiling point of 87 to 90° C./80 mmHg as a fraction. The yield was 87%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 17.82 | 53.30 | 20.96 | 7.92 |
| Found (%) | 17.79 | 53.37 | 20.91 | 7.93 |

GC-MS
m/e (M+) molecular weight: 606.
Infrared absorption spectrum

A chart of the infrared absorption spectrum is shown in FIG. 1. From this chart, it is recognized that the absorption at 1890 cm$^{-1}$ caused by

disappeared and an absorption at 1785 cm$^{-1}$ caused by

appeared newly.
$^{19}$F-NMR
δ(ppm): −66.5 (m, 1F, CF);
−52. 8 (m, 2F, CF$_2$);
−41.0 (m, 1F, CF-COI);
−7.1 to 1.5 (m, 13F, —CF$_3$, CF$_2$O—).

From the above results of the measurement, it was confirmed that the product was a carboxylic acid iodide represented by the following formula:

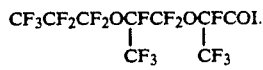

EXAMPLE 2

200 g (0.33 mol) of the carboxylic acid iodide obtained in Example 1 was charged into an ultraviolet irradiating apparatus equipped with a high-pressure mercury lamp ( λ=220 to 380 nm) having a quartz cooling tube and while the carboxylic acid iodide was stirred with a magnetic stirrer, it was irradiated with ultraviolet light. The reaction was performed at 35° to 40° C. for 16 hours using the 100-W high-pressure mercury lamp under a flow of argon. After the completion of the reaction, the reaction product was distilled to obtain 181 g of a fraction at 78.5° C./101 mmHg. The yield was 95%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 16.61 | 55.88 | 21.79 | 5.54 |
| Found (%) | 16.57 | 55.91 | 21.92 | 5.60 |

GC-MS
m/e (M+) molecular weight: 578.
Infrared absorption spectrum

Figure 2:
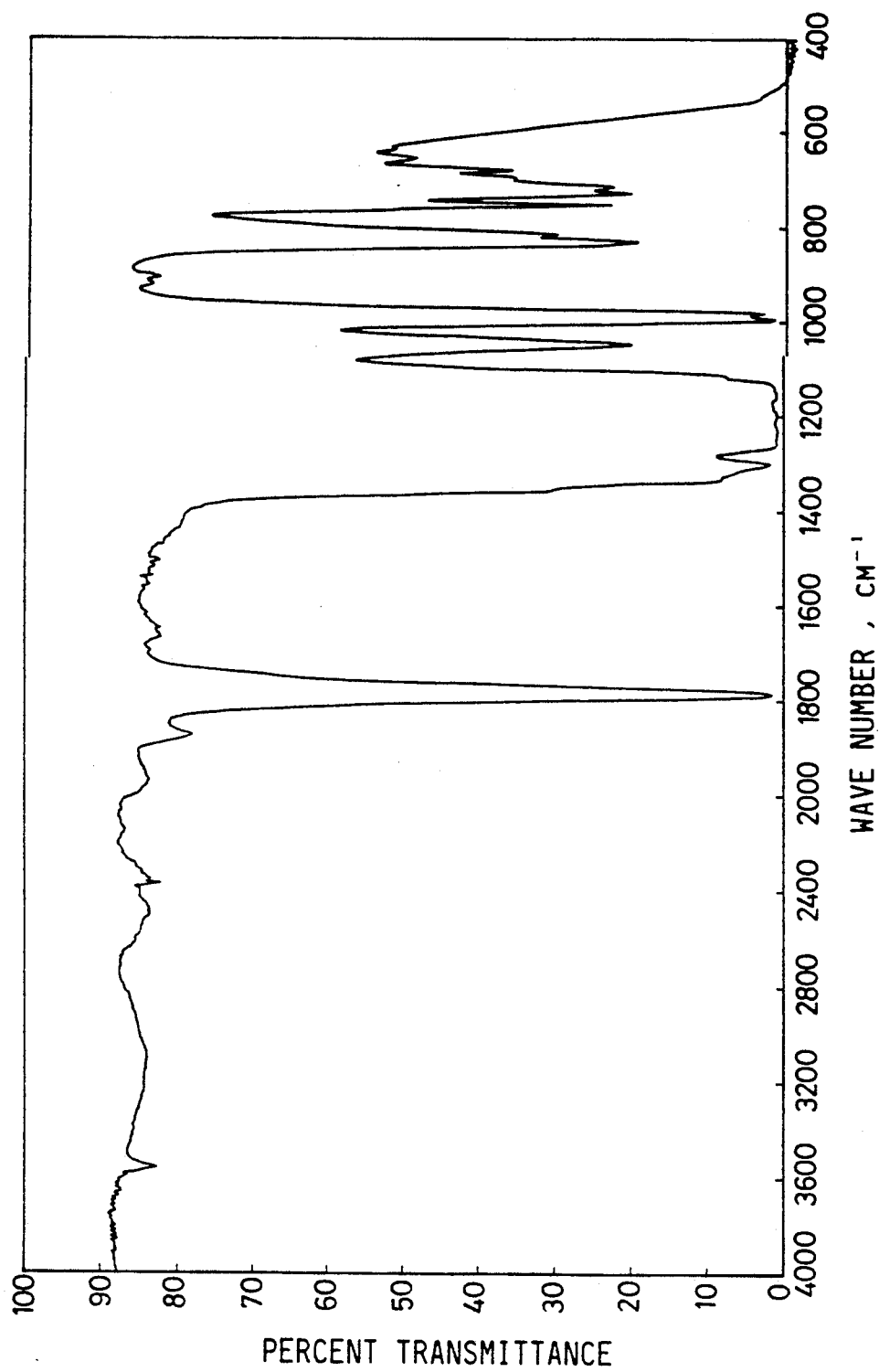
FIG. 2 is the infrared absorption spectrum of Example 2.

A chart of the infrared absorption spectrum is shown in FIG. 2. From this chart, it was recognized that the absorption at 1185 cm$^{-1}$ caused by

disappeared.
$^{19}$F-NMR
δ(ppm): −69.9 (m, 1F, CF);
−59.8 (m, 2F, CF$_2$);
−3.7 to −15.8 (m, 13F, —CF$_3$, CF$_2$O—);
0.3 (m, 1F, —CFI).

From the above results of the measurement, it was confirmed that the product was a compound represented by the following formula:

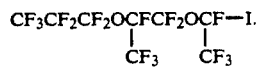

EXAMPLE 3

A mechanical stirrer, a reflux condenser, and a gas introducing tube were attached to a four-necked flask with an internal volume of 0.5 l. 332 g (1.0 mol) of a carboxylic acid fluoride represented by the following formula:

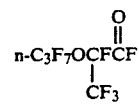

and 5 g of acetonitrile were charged into the flask. While the contents were stirred, 141 g (1.1 mol) of lithium iodide was added thereto in portions little by little under a flow of argon. At that time, the amount of the lithium iodide added was controlled so that the temperature of the contents might not exceed 40° C. After the completion of the addition, the contents were stirred for about 15 hours.

Then the contents were filtered through a glass filter to remove the solids. The obtained liquid was distilled to obtain 398 g of a product having a boiling point of 30 to 32° C./60 mmHg as a fraction. The yield was 90%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 16.36 | 47.50 | 28.86 | 7.27 |
| Found (%) | 16.33 | 47.41 | 28.95 | 7.31 |

GC-MS m/e (M+) molecular weight: 440.

Infrared absorption spectrum

Figure 3:
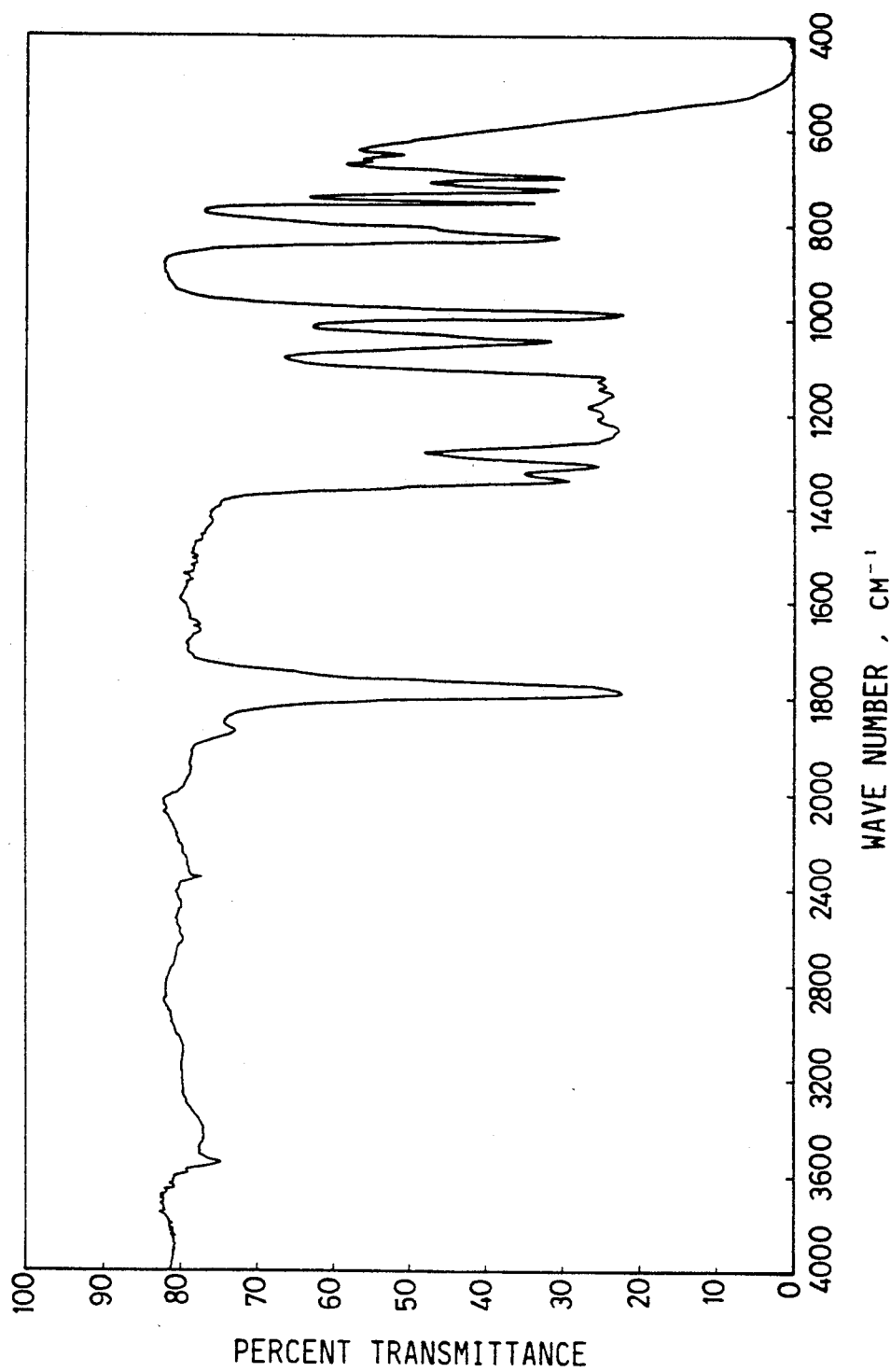
FIG. 3 is the infrared absorption spectrum of Example 3.

A chart of the infrared absorption spectrum is shown in FIG. 3. From this chart, it is recognized that the absorption at 1890 cm$^{-1}$ caused by

disappeared and an absorption at 1785 cm$^{-1}$ caused by

appeared newly.

$^{19}$F-NMR

δ(ppm): −52.8 (m, 2F, CF$_2$);
−41.5 (m, 1F, CFCOI);
−7.1 to 1.2 (m, 5F, CF$_3$, CF$_2$O).

From the above results of the measurement, it was confirmed that the product was a carboxylic acid iodide represented by the following formula:

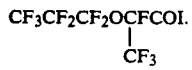

EXAMPLE 4

200 g (0.45 mol) of the carboxylic acid iodide obtained in Example 3 was charged into an ultraviolet irradiating apparatus equipped with a high-pressure mercury lamp ( λ=220 to 380 nm) having a quartz cooling tube and while the carboxylic acid iodide was stirred with a magnetic stirrer, it was irradiated with ultraviolet light. The reaction was performed at 25° to 35° C. for 20 hours using the 100-W high-pressure mercury lamp under a flow of argon. After the completion of the reaction, the reaction product was distilled to obtain 158 g of a fraction at 86° to 88° C. The yield was 84%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 14.56 | 50.73 | 30.83 | 3.88 |
| Found (%) | 14.63 | 50.82 | 30.61 | 3.94 |

GC-MS m/e (M+) molecular weight: 412.

Infrared absorption spectrum

Figure 4:
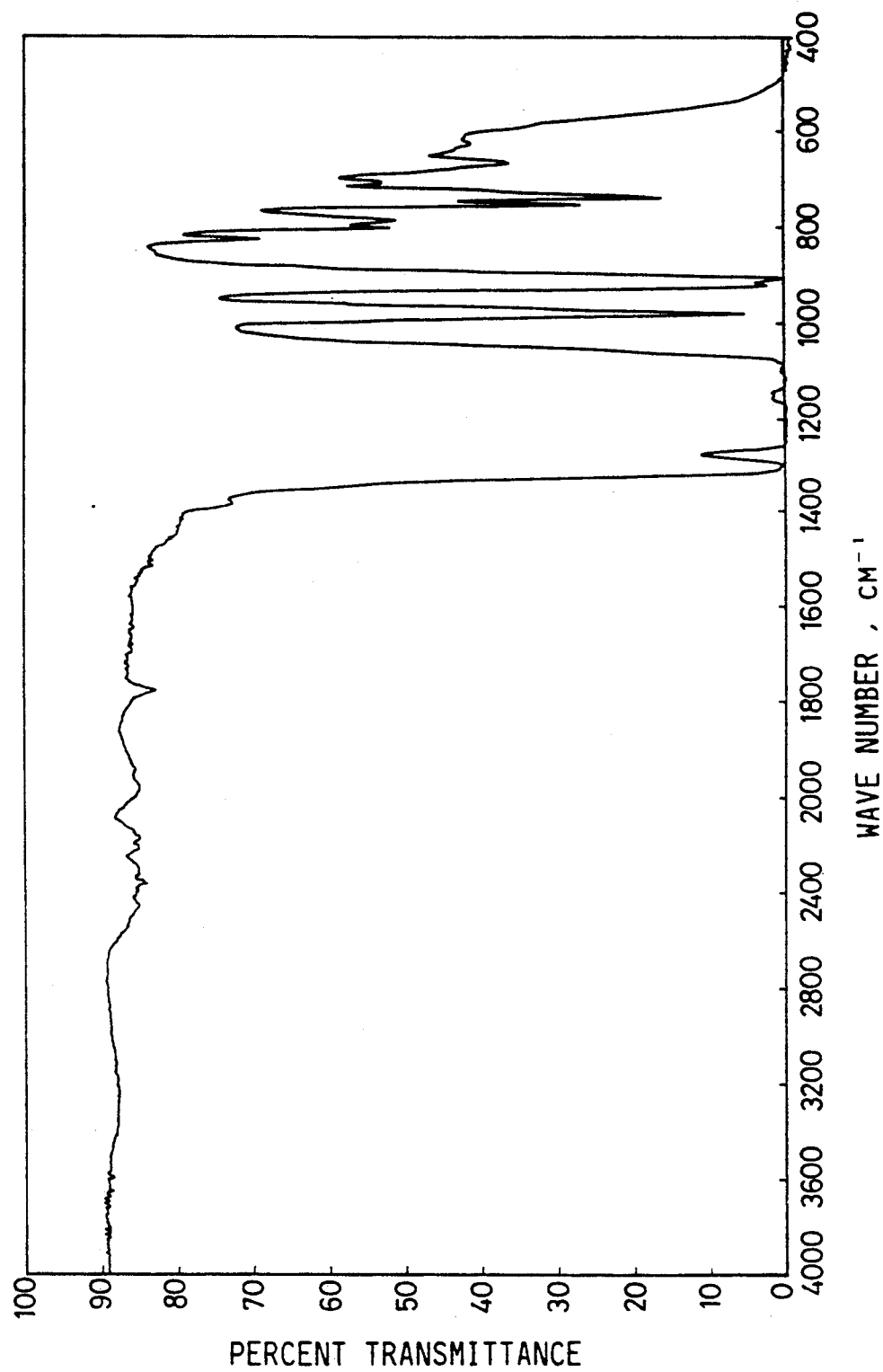
FIG. 4 is the infrared absorption spectrum of Example 4.

A chart of the infrared absorption spectrum is shown in FIG. 4. From this chart, it was recognized that the absorption at 1785 cm$^{-1}$ caused by

disappeared.

$^{19}$F-NMR

δ(ppm): −53.6 (m, 2F, —CF$_2$—);
−11.3 to −5.3 (m, 5F, CF$_2$O, CF—CF$_3$);
−5.2 (m, 3F, CF$_3$, CF$_2$);
0.5 (m, CF—I).

From the above results of the measurement, it was confirmed that the product was a compound represented by the following formula:

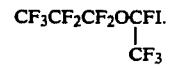

EXAMPLE 5

A mechanical stirrer, a reflux condenser, and a gas introducing tube were attached to a four-necked flask with an internal volume of 0.5 l. 332 g (0.50 mol) of a carboxylic acid fluoride represented by the following formula:

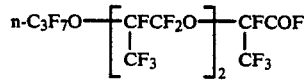

and 2 g of acetonitrile were charged into the flask. While the contents were stirred, 73.6 g (0.55 mol) of lithium iodide was added thereto in portions little by little under a flow of argon. At that time, the amount of the lithium iodide added was controlled so that the temperature of the contents might not exceed 40° C. After the completion of the addition, the contents were stirred for about 8 hours.

Then the contents were filtered through a glass filter to remove the solids thereby obtaining a liquid product in an amount of 341 g. The yield was 88%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 18.65 | 56.61 | 16.45 | 8.29 |
| Found (%) | 18.54 | 56.59 | 16.51 | 8.36 |

GC-MS m/e (M+) molecular weight: 772.

Infrared absorption spectrum

Figure 5:
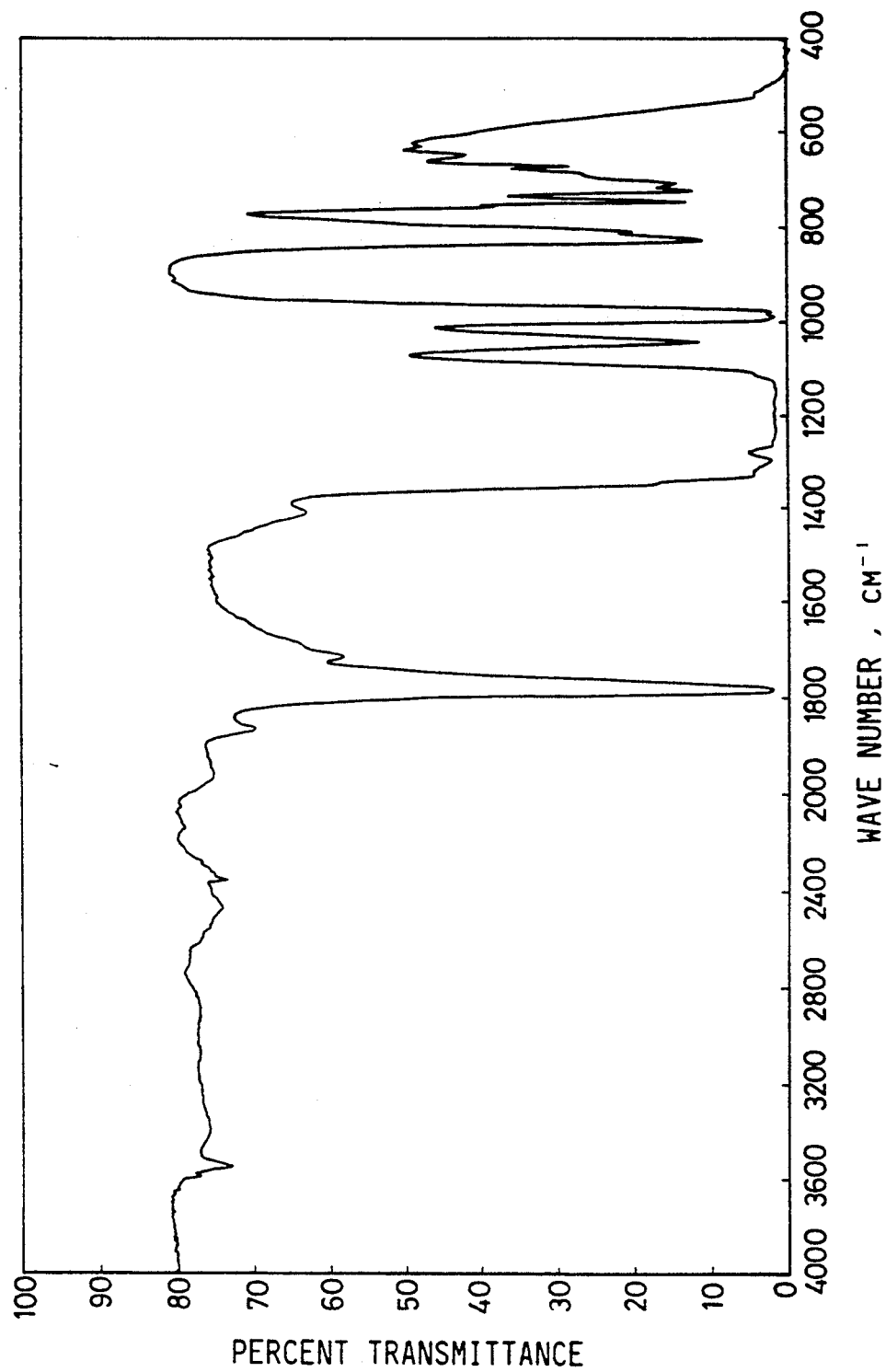
FIG. 5 is the infrared absorption spectrum of Example 5.

A chart of the infrared absorption spectrum is shown in FIG. 5. From this chart, it is recognized that the absorption 1890 cm$^{-1}$ caused by

disappeared and an absorption at 1785 cm$^{-1}$ caused by

appeared newly.

$^{19}$F-NMR

δ(ppm): −68.4 (m, 2F, CF);
−53.1 (m, 2F, CF$_2$);

—42.3 (m, 1F, —FCOI);
—10.0 to 3.3 (m, 18F, —CF$_3$, CF$_2$O).

From the above results of the measurement, it was confirmed that the product was a carboxylic acid iodide represented by the following formula:

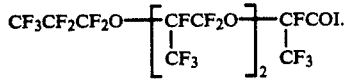

EXAMPLE 6

200 g (0.26 mol) of the carboxylic acid iodide obtained in Example 5 was charged into an ultraviolet irradiating apparatus equipped with a high-pressure mercury lamp ($\lambda$=220 to 380 nm) having a quartz cooling tube and while the carboxylic acid iodide was stirred with a magnetic stirrer, it was irradiated with ultraviolet light. The reaction was performed at 35° to 40° C. for 25 hours using the 100-W high-pressure mercury lamp under a flow of argon. After the completion of the reaction, the reaction product was distilled to obtain 181 g of a fraction at 72° C./20 mmHg. The yield was 93%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 17.74 | 58.74 | 17.07 | 6.45 |
| Found (%) | 17.51 | 58.81 | 17.03 | 6.65 |

GC-MS
m/e (M+) molecular weight: 744.
Infrared absorption spectrum

Figure 6:
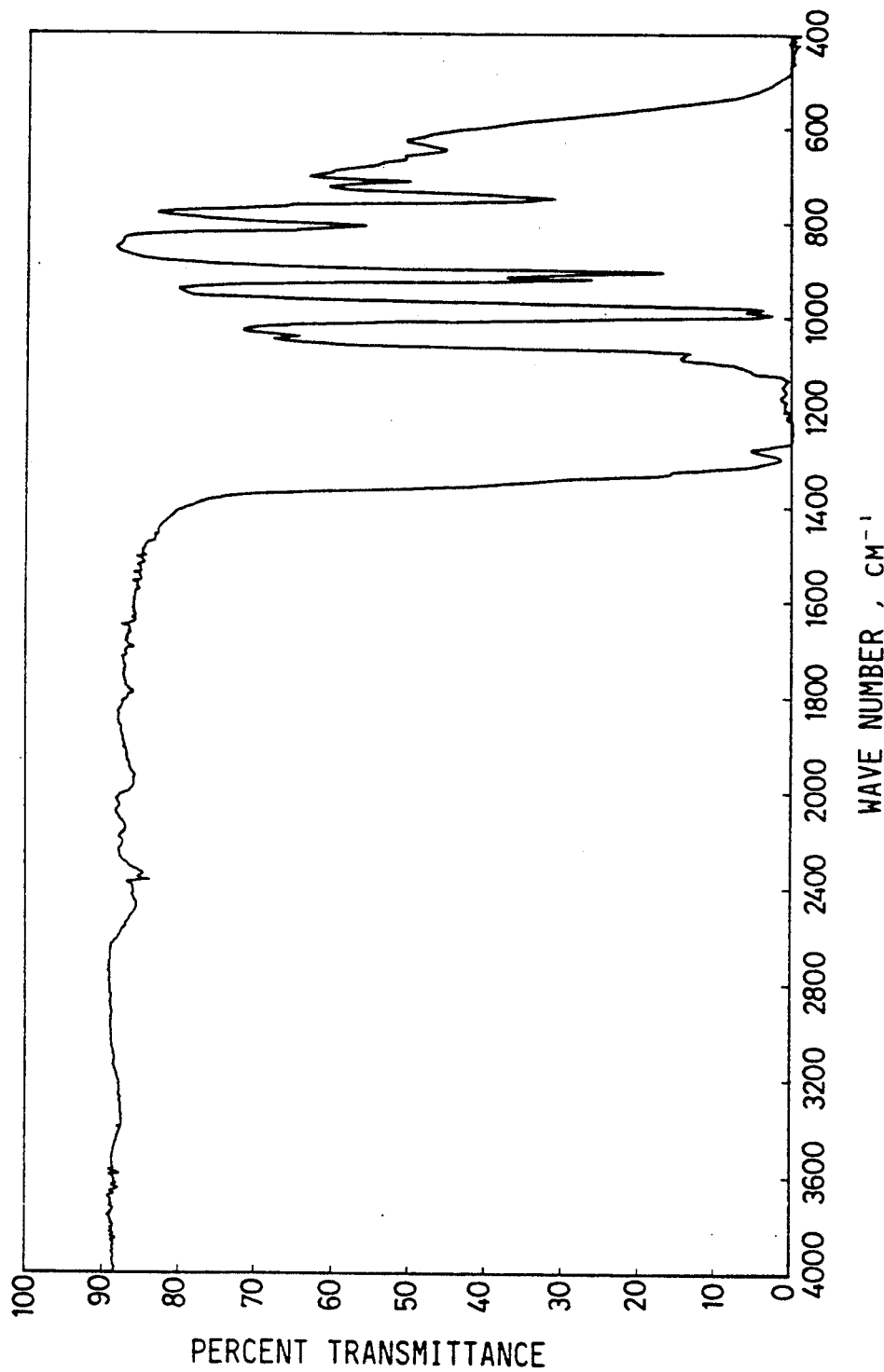
FIG. 6 is the infrared absorption spectrum of Example 6.

A chart of the infrared absorption spectrum is shown in FIG. 6. From this chart, it was recognized that the absorption at 1785 cm$^{-1}$ caused by

disappeared.
$^{19}$F-NMR
$\delta$(ppm): —68.0 (m, 2F, CF);
—53.5 (m, 2F, CF$_2$);
—13.8 to —0.7 (m, 18F, CF$_3$, CF$_2$O);
—1.6 (m, 1F, CFI).

From the above results of the measurement, it was confirmed that the product was a compound represented by the following formula:

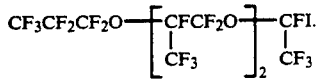

EXAMPLE 7

A mechanical stirrer, a reflux condenser, and a gas introducing tube were attached to a four-necked flask with an internal volume of 0.5 l. 350 g (0.82 mol) of a dicarboxylic acid difluoride represented by the following formula:

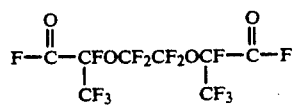

and 7 g of acetonitrile were charged into the flask. While the contents were stirred, 242 g (1.80 mol) of lithium iodide was added thereto in portions little by little under a flow of argon. At that time, the amount of the lithium iodide added was controlled so that the temperature of the contents might not exceed 50° C. After the completion of the addition, the contents were stirred for about 3 hours.

Then the contents were filtered through a glass filter to remove the solids. The obtained liquid was distilled to obtain 461 g of a product having a boiling point of 83° C./5 mmHg as a fraction. The yield was 87%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 14.95 | 35.51 | 39.56 | 9.96 |
| Found (%) | 14.75 | 35.60 | 39.63 | 10.09 |

GC-MS
m/e (M+) molecular weight: 642.
Infrared absorption spectrum

Figure 7:
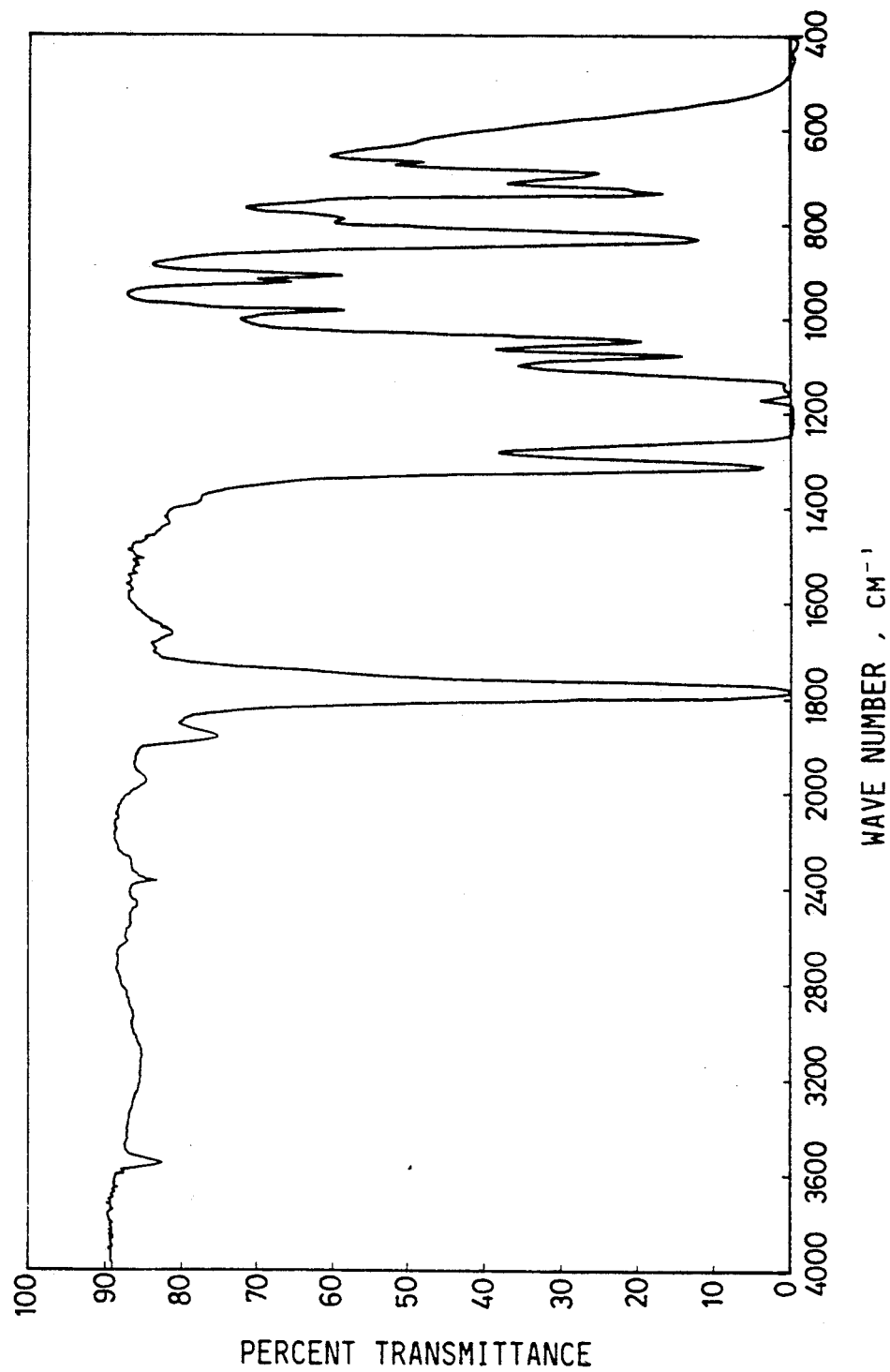
FIG. 7 is the infrared absorption spectrum of Example 7.

A chart of the infrared absorption spectrum is shown in FIG. 7. From this chart, it is recognized that the absorption at 1890 cm$^{-1}$ caused by

disappeared and an absorption at 1785 cm$^{-1}$ caused by

appeared newly.
$^{19}$F-NMR
$\delta$(ppm): —44.4 (m, 2F, CF);
—8.3 (m, 4F, CF$_2$);
—5.1 (m, 6F, —CF$_3$);

From the above results of the measurement, it was confirmed that the product was a dicarboxylic acid diiodide represented by the following formula:

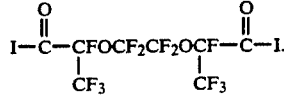

EXAMPLE 8

200 g (0.31 mol) of the dicarboxylic acid diiodide obtained in Example 7 was charged into an ultraviolet irradiating apparatus equipped with a high-pressure mercury lamp ( λ=220 to 380 nm) having a quartz cooling tube and while the dicarboxylic acid diiodide was stirred with a magnetic stirrer, it was irradiated with ultraviolet light. The reaction was performed at 35° to 40° C. for 28 hours using the 100-W high-pressure mercury lamp under a flow of argon. After the completion of the reaction, the reaction product was distilled to obtain 156 g of a fraction at 95° C./100 mmHg. The yield was 85%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 12.29 | 38.91 | 43.34 | 5.46 |
| Found (%) | 12.38 | 38.97 | 43.56 | 5.31 |

GC-MS m/e (M+) molecular weight: 586.

Infrared absorption spectrum

Figure 8:
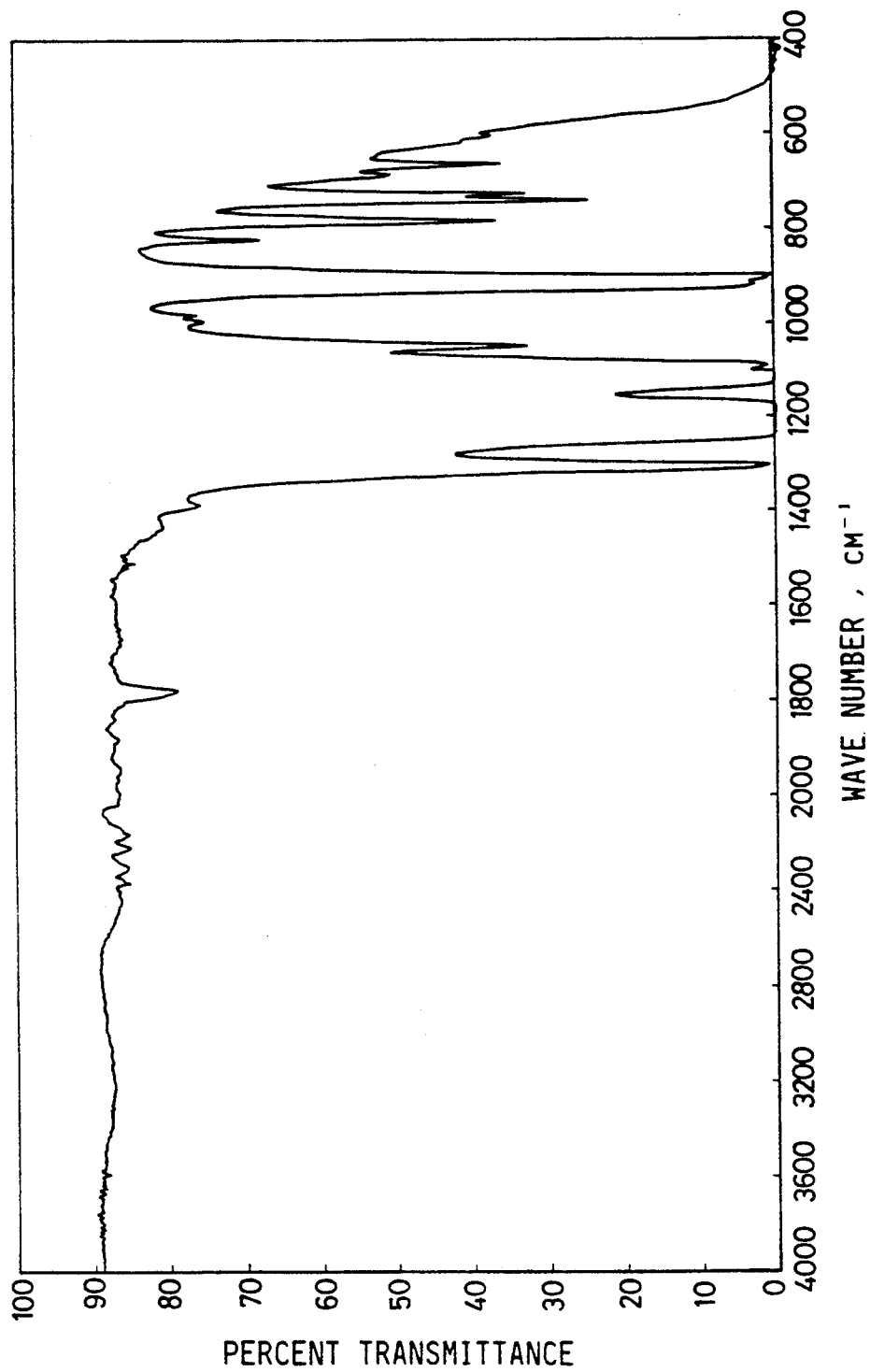
FIG. 8 is the infrared absorption spectrum of Example 8.

A chart of the infrared absorption spectrum is shown in FIG. 8. From this chart, it was recognized that the absorption at 1785 cm$^{-1}$ caused by $$-\overset{O}{\underset{\|}{C}}-I$$

disappeared.

$^{19}$F-NMR

δ(ppm) −14.3 (m, 4F, CF$_2$);
−8.2 (m, 6F, CF$_3$);
0.9 (m, 2F, CF).

From the above results of the measurement, it was confirmed that the product was a compound represented by the following formula:

$$I-CFOCF_2CF_2OCF-I.$$
$$\phantom{I-}CF_3\phantom{OCF_2CF_2O}CF_3$$

so that the temperature of the contents might not exceed 50° C. After the completion of the addition, the contents were stirred for about 12 hours.

Then the contents were filtered through a glass filter to remove the solids, thereby obtaining 398 g of a liquid product. The yield was 92%.

With respect to the obtained product, the elementary analysis and the measurement of GC-MS, infrared absorption spectrum, and $^{19}$F-NMR were carried out. The results are shown below.

| Elementary analysis | | | | |
|---|---|---|---|---|
| | C | F | I | O |
| Calculated (%) | 17.89 | 50.00 | 22.28 | 9.82 |
| Found (%) | 17.72 | 49.83 | 22.49 | 9.96 |

GC-MS m/e (M+) molecular weight: 1140.

Infrared absorption spectrum

Figure 9:
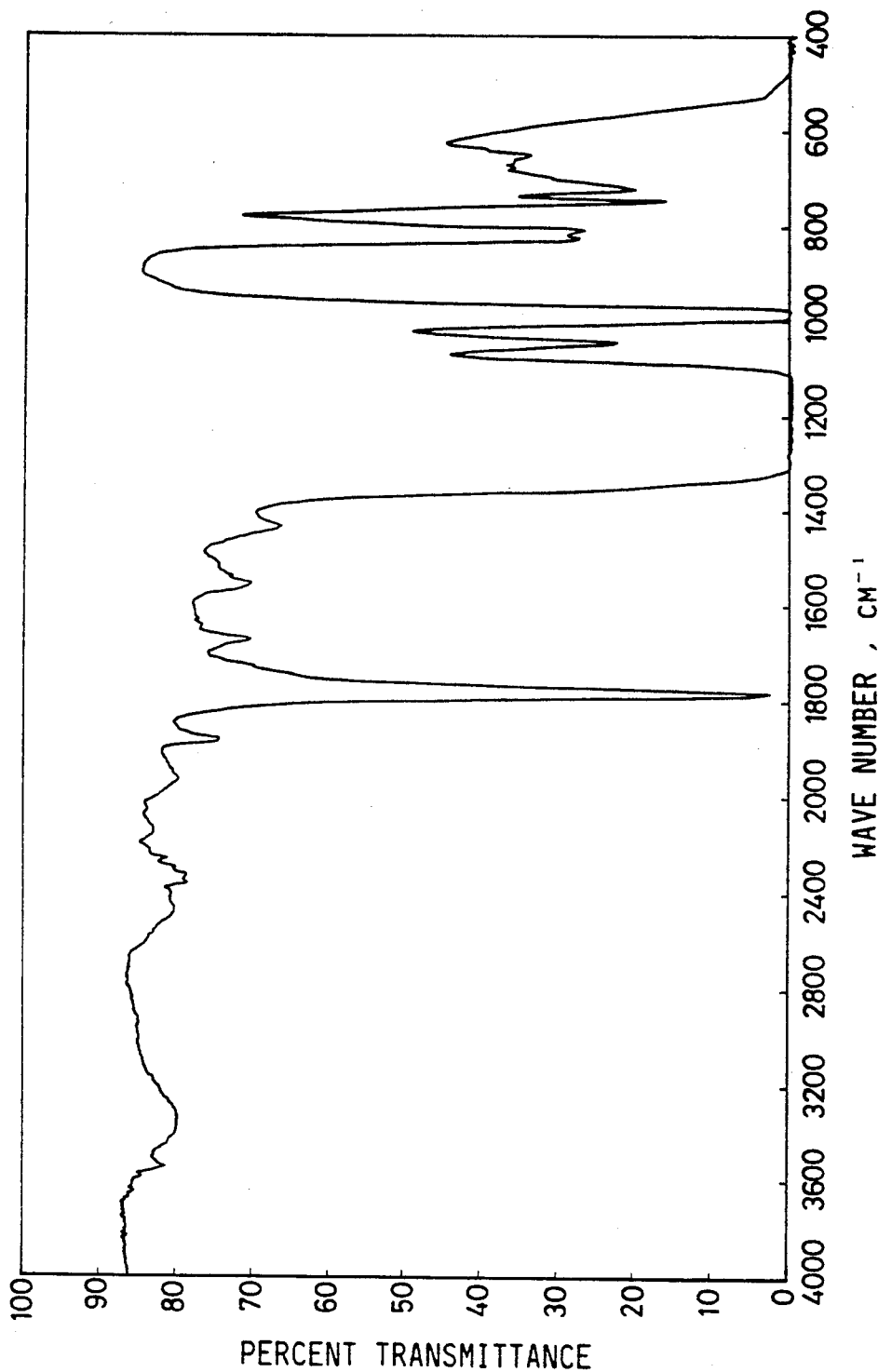
FIG. 9 is the infrared absorption spectrum of Example 9.

A chart of the infrared absorption spectrum is shown in FIG. 9. From this chart, it is recognized that the absorption at 1890 cm$^{-1}$ caused by $$-\overset{O}{\underset{\|}{C}}-F$$

disappeared and an absorption at 1785 cm$^{-1}$ caused by $$-\overset{O}{\underset{\|}{C}}-I$$

appeared newly.

$^{19}$F-NMR

δ(ppm): −68.9 (m, 3F, CFO);
−44.7 (m, 2F, CFCOI);
−11.2 to −3.3 (m, 25F, CF$_3$, CF$_2$).

From the above results of the measurement, it was confirmed that the product was a dicarboxylic acid diiodide represented by the following formula:

$$I-\overset{O}{\underset{\|}{C}}-\underset{CF_3}{\underset{|}{CF}}-\left[\underset{CF_3}{\underset{|}{OCF_2CF}}\right]_a-OCF_2CF_2O-\left[\underset{CF_3}{\underset{|}{CFCF_2O}}\right]_b-\underset{CF_3}{\underset{|}{CF}}-\overset{O}{\underset{\|}{C}}-I$$

wherein a+b=3.

EXAMPLE 9

A mechanical stirrer, a reflux condenser, and a gas introducing tube were attached to a four-necked flask with an internal volume of 0.5 l. 350 g (0.38 mol) of a dicarboxylic acid difluoride represented by the following formula:

$$F-\overset{O}{\underset{\|}{C}}-\underset{CF_3}{\underset{|}{CF}}-\left[\underset{CF_3}{\underset{|}{OCF_2CF}}\right]_a-OCF_2CF_2O-\left[\underset{CF_3}{\underset{|}{CFCF_2O}}\right]_b-\underset{CF_3}{\underset{|}{CF}}-\overset{O}{\underset{\|}{C}}-F$$

wherein a+b=3 and 7 g of acetonitrile were charged into the flask. While the contents were stirred, 116.6 g (0.83 mol) of lithium iodide was added thereto in portions little by little under a flow of argon. At that time, the amount of the lithium iodide added was controlled

EXAMPLE 10

200 g (0.18 mol) of the dicarboxylic acid diiodide obtained in Example 9 was charged into an ultraviolet irradiating apparatus equipped with a high-pressure mercury lamp ( λ=220 to 380 nm) having a quartz cooling tube and while the dicarboxylic acid diiodide was stirred with a magnetic stirrer, it was irradiated with ultraviolet light. The reaction was performed at 35° to 40° C. for 18 hours using the 100-W high-pressure mercury lamp under a flow of argon. After the completion of the reaction, the reaction product was distilled to obtain 178 g of a fraction at 110° C./3 mmHg. The yield was 90%.

With respect to the obtained product, the elementary analysis and the measurement of GC-MS, infrared absorption spectrum, and $^{19}$F-NMR were carried out. The results are shown below.

| Elementary analysis | C | F | I | O |
|---|---|---|---|---|
| Calculated (%) | 16.61 | 52.58 | 23.43 | 7.38 |
| Found (%) | 16.49 | 52.65 | 23.41 | 7.45 |

GC-MS m/e (M+) molecular weight: 1084.

Infrared absorption spectrum

Figure 10:
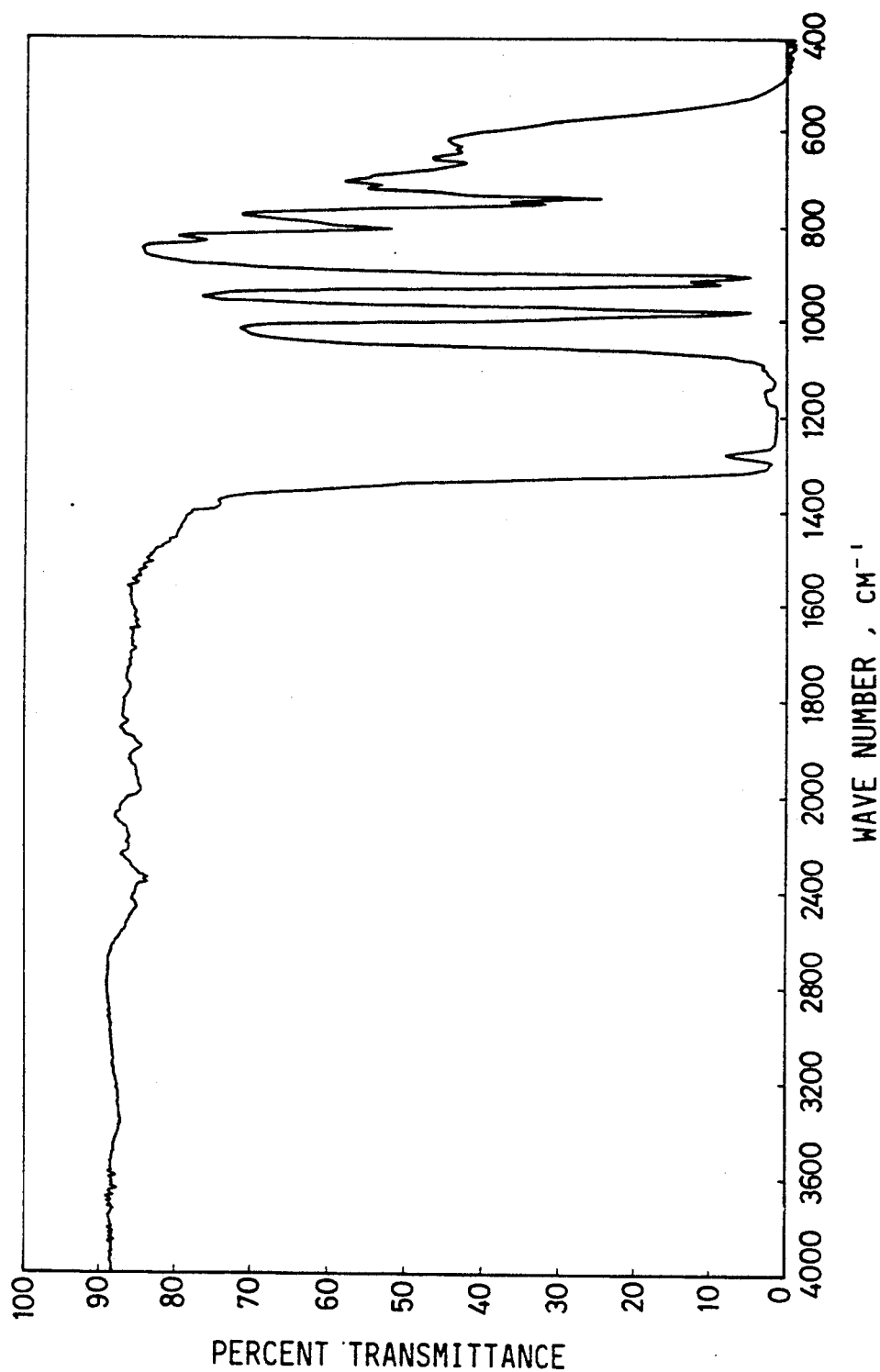
FIG. 10 is the infrared absorption spectrum of Example 10.

A chart of the infrared absorption spectrum is shown in FIG. 10. From this chart, it was recognized that the absorption at 1785 cm$^{-1}$ caused by

disappeared.

$^{19}$F-NMR

δ(ppm): −69.2 (in, 3F, CFO);
−15.5 to −5.0 (m, 25F, CF$_3$, CF$_2$);
−1.0 (m, 2F, CFI).

From the above results of the measurement, it was confirmed that the product was a compound represented by the following formula:

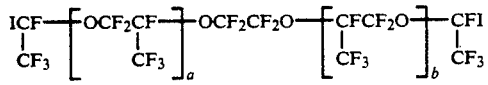

wherein a+b=3.

What is claimed is:

1. An oligohexafluoropropylene oxide derivative represented by the general formula (I):

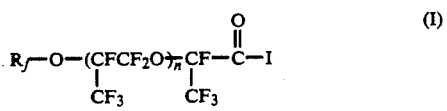

wherein R$_f$ represents a perfluoroalkyl group having 1 to 10 carbon atoms and n is an integer of 0 to 100.

2. An oligohexafluoropropylene oxide derivative as claimed in claim 1, wherein R$_f$ represents a trifluoromethyl group, a pentafluoroethyl group, a heptafluoropropyl group, or a heptafluoroisopropyl group, and n is an integer of 0 to 30.

3. An oligohexafluoropropylene oxide derivative represented by the general formula (II):

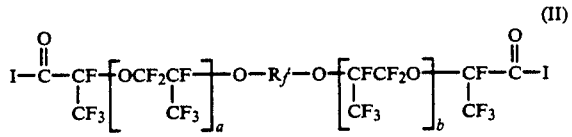

wherein R$_f'$ represents a perfluoroalkylene group having 2 to 10 carbon atoms and a and b are each independently an integer of 0 to 20.

4. An oligohexafluoropropylene oxide derivative as claimed in claim 3, wherein R$_f'$ represents —CF$_2$CF$_2$—, —CF$_2$CF$_2$CF$_2$—, —CF$_2$CF$_2$CF$_2$CF$_2$—or —CF$_2$CF$_2$CF$_2$CF$_2$CF$_2$—, and a and b are each independently an integer of 0 to 10.

5. An oligohexafluoropropylene oxide derivative as claimed in claim 1, wherein R$_f$ is a heptafluoropropyl group and n is selected from the group consisting of 0, 1 and 2.

6. An oligohexafluoropropylene oxide derivative as claimed in claim 3 wherein R$_f'$ is —CF$_2$CF$_2$— and a=b=0.

7. An oligohexafluoropropylene oxide derivative as claimed in claim 3 wherein R$_f'$ is —CF$_2$CF$_2$— a+b=3.

* * * * *